(12) United States Patent
Ruf et al.

(10) Patent No.: US 9,372,163 B2
(45) Date of Patent: Jun. 21, 2016

(54) METHOD OF CONDUCTING AN X-RAY DIFFRACTION-BASED CRYSTALLOGRAPHY ANALYSIS

(71) Applicant: Bruker AXS, Inc., Madison, WI (US)

(72) Inventors: Michael Ruf, Madison, WI (US); Joerg Kaercher, Madison, WI (US); Bruce C Noll, Madison, WI (US)

( * ) Notice: Subject to any disclaimer, the term of this patent is extended or adjusted under 35 U.S.C. 154(b) by 149 days.

(21) Appl. No.: 14/166,286

(22) Filed: Jan. 28, 2014

(65) Prior Publication Data

US 2015/0276629 A1 Oct. 1, 2015

(51) Int. Cl.
*G01N 23/207* (2006.01)
*G01N 23/205* (2006.01)
*G01N 23/20* (2006.01)

(52) U.S. Cl.
CPC ...... *G01N 23/2055* (2013.01); *G01N 23/20016* (2013.01); *G01N 23/20075* (2013.01)

(58) Field of Classification Search
CPC ............................ G01N 23/20; G01N 23/207
USPC ..................................... 378/71, 73
See application file for complete search history.

(56) References Cited

U.S. PATENT DOCUMENTS 7,649,974 B2 * 1/2010 Arenson et al. ................. 378/16
2006/0067470 A1 * 3/2006 Wang et al. ..................... 378/73

OTHER PUBLICATIONS

Daniel Gewirth, "The HKL Manual A description of the programs Denzo Xdisplayf Scalepack an Oscillation Data Processing Suite for Macromolecular Crystallography", Sep. 1, 2003, "http://www.hkl-xray.com/sites/default/files/manual_online.pdf".
Dauter et al, "Efficient use of synchrotron radiation for macromolecular diffraction data collection", Progress in Biophysics and Molecular Biology, Pergamon Press, Oct. 1, 2005, vol. 89, No. 2, pp. 153-172, Oxford, GB.
Petratos et al, "The crystal structure of apo-pseudoazurin from Alcaligenes faecalis S-6", FEBS Letter, Elsevier, Jul. 24, 1995, vol. 368, No. 3, pp. 432-434, Amsterdam, NL.
Lawrence M.C. et al, "The Three-dimensional Structure of the Bifunctional 6-Hydroxymethyl-7, 8-Dihydropterin Pyrophosphokinase/Dihydropteroate Synthase of *Saccharomyces cerevisiae*", Journal of Molecular Biology, Academic Press, May 6, 2005, vol. 348, No. 3, pp. 655-670, United Kingdom.

* cited by examiner

*Primary Examiner* — Jurie Yun
(74) *Attorney, Agent, or Firm* — Benoit & Cote, Inc.; Philip Conrad

(57) ABSTRACT

A method of X-ray diffraction-based analysis for determining the structure of a crystal sample is provided. The method comprises conducting pre-experiment to collect a first set of diffraction images including reflections at corresponding intensities. The method also comprises conducting a main experiment to collect a second set of diffraction images, the diffraction images of the second set including the reflections with higher relative intensities than those produced during the first experiment, at least some of the diffraction images of the second set including topped reflections resulting from detector saturation. The method also includes a step of replacing intensities of the topped reflections from the second set of images with intensities obtained for the corresponding reflections from the first set of images.

21 Claims, 3 Drawing Sheets

METHOD OF CONDUCTING AN X-RAY DIFFRACTION-BASED CRYSTALLOGRAPHY ANALYSIS

BACKGROUND OF THE INVENTION

1. Field of the Invention

This invention relates generally to the field of X-ray diffraction and, more specifically, to the processing of topped reflections in the data collected for determining the structure of a crystalline compound.

2. Description of the Related Art

Single-crystal X-ray diffraction (SC-XRD) is a method for determining the three-dimensional atomic structure of a crystalline compound. A single-crystal specimen of the compound is irradiated with monochromatic X-ray radiation from different directions, some of which is diffracted in specific patterns and detected by an X-ray detector. The structural information of the specimen is determined from the geometry and relative intensities of these diffraction patterns. The intensities are integrated from the pixels in the X-ray detector images.

A typical laboratory system 100 for performing single-crystal diffraction experiments consists of five components as shown in FIG. 1. The components include an X-ray source 102 that produces a primary X-ray beam 104 with the required radiation energy, focal spot size and intensity. X-ray optics 106 are provided to condition the primary X-ray beam 104 to a conditioned, or incident, beam 108 with the required wavelength, beam focus size, beam profile and divergence. A goniometer 110 is used to establish and manipulate geometric relationships between the incident X-ray beam 108, the crystal sample 112 and the X-ray sensor 114. The incident X-ray beam 108 strikes the crystal sample 112 and produces scattered X-rays 116 which are recorded in the sensor 114. A sample alignment and monitor assembly comprises a sample illuminator 118 that illuminates the sample 112 and a sample monitor 120, typically a video camera, which generates a video image of the sample to assist users in positioning the sample in the instrument center and monitoring the sample's state and position.

The goniometer 110 allows the crystal sample 112 to be rotated around several axes. Precise crystallography requires that the sample crystal 112 be aligned to the center of the goniometer 110 and maintained in that center when rotated around the goniometer rotational axes during data collection. During exposure, the sample (a single crystal of the compound of interest) is rotated in the X-ray beam 108 through a precise angular range with a precise angular velocity. The purpose of this rotation is to predictably bring Bragg reflections into constructive interference. At each rotational position, the sensor captures an image of the diffracted X-ray signals. The result of such an X-ray diffraction experiment is thus a set of 2D images whose pixels indicate the locations and the intensities of the individual reflections.

A crystalline compound has a continuous distribution of electrons. When incident X-rays hit the compound, they are diffracted with a specific diffraction pattern by the electrons. The diffracted X-rays create reflections in the 2D images captured by the detector 114. The diffraction pattern of the reflections is related to the density map of electrons of the compound by a Fourier Transform. Based on the location of the reflections within the set of 2D images, and based on the intensities of the pixels defining the reflections, a reciprocal sphere of data may be generated, with discrete reflections being positioned, one relative to the other, in the reciprocal sphere, the intensity of each reflection being a coefficient of the Fourier transform. The relative intensities of the reflections in turn yield information about the arrangement of the electrons in the crystal structure. Applying an inverse Fourier Transform to the 3D reciprocal sphere data provides the electron density map, which is in turn indicative of the structure of the crystalline compound.

FIG. 2 shows typical steps conducted during an X-ray diffraction experiment. The experiment typically starts with conducting a pre-experiment (step 200) to collect a few diffraction images, sufficient to determine the appropriate data collection parameters for the main experiment. Deciding on the proper data collection parameters to use in the main experiment will depend on the unit cell of the crystal sample, its mosaicity, the signal-to-noise ratio I/sigma(I), where sigma is the standard deviation) to achieve for a given resolution, the diffraction limit and the orientation matrix of the experiment set-up, which are all determined during the pre-scan experiment. The pre-experiment allows, for example, a determination of the optimized exposure time to use for each image captured by the detector in the main experiment. With slow acquisition speeds and long dead time of traditional diffraction systems, typically, only partial data is collected during the pre-experiment.

When conducting the main X-ray diffraction experiment (step 202), the exposure time of the X-ray detector is selected to allow detection of both stronger and weaker intensity reflections. However, even if the exposure time is optimized using information about the intensity distribution obtained during pre-experiment (step 200), stronger reflections will saturate some of the pixels of the detector during the main experiment. In other words, even with optimized parameters, some of the reflection signals will extend beyond the dynamic range of the X-ray detector, resulting in inaccurate data collected for these reflections. These reflections are often referred to as "topped" or "overload" reflections. The correct intensity of these topped signals cannot be recorded correctly and needs to be reconstructed from additional images. As such, known methods require that while conducting the main experiment, each image is verified in order to determine whether or not saturated pixels are present in an image (step 204).

Traditionally, the intensity data of saturated pixels was either discarded or a new image frame was captured during a second exposure, with higher scan speed and shorter exposure time, or with an attenuated X-ray beam (step 206). Both measures reduce the intensity of the signal, such that it falls in the dynamic range of the detector. The intensity of the pixels that had saturated in the original image is replaced with a scaled intensity of the pixels of the second exposure and a composite image is built based on the two images resulting from the first and second exposures (step 208). The conventional method is time-consuming since the images must be read and analyzed during the main experiment to determine whether saturated pixels are present or not. If saturated pixels are present, the goniometer must be stopped, the intensity of the beam needs to be attenuated and/or the exposure time must be reduced in order to capture a second image without any saturated pixels.

The result of the diffraction experiment is a set of many diffraction images (210) with pixels containing intensities of the reflections. The intensities of each reflection are then integrated, scaled, and normalized (steps 212, 214). The output data provide a location and intensity for each reflection in the reciprocal space (216). The output data can then be used to determine the electron density map of the sample by applying an inverse Fourier transform. The electron density map in turn allows one to determine the structure of the crystalline sample.

SUMMARY OF THE INVENTION

In accordance with the present invention, a method of X-ray diffraction-based analysis for determining the structure of a crystal sample is provided. In an exemplary embodiment, the method includes a step of conducting a first experiment during which the sample is irradiated with an X-ray beam and a first set of diffraction images is collected by an X-ray detector, the diffraction images including reflections at corresponding intensities. The method also includes a step of conducting a second experiment during which the sample is irradiated by an X-ray beam and a second set of diffraction images is collected. The diffraction images of the second set include the reflections with higher relative intensities than those produced during the first experiment, at least some of the diffraction images of the second set including topped reflections resulting from detector saturation. The method also includes a step of replacing intensities of the topped reflections from the second set of images with intensities obtained for the corresponding reflections from the first set of images.

The first experiment may be conducted in a single scan, with angular speed of three degrees/sec or less. The second set of diffraction images can be collected during several scans of the crystal sample. An angular speed of one degree/sec or less is generally used for the second experiment. The first experiment may be a pre-experiment and the second experiment, a main experiment, the pre-experiment being conducted prior to the main experiment.

In one embodiment, the method uses a lower rotational speed of the crystal sample when conducting the second experiment, relative to the rotational speed used for the first experiment. Alternatively, the exposure time of the X-ray detector can be longer when capturing the second set of diffraction images, relative to the exposure time used for the first set of images. It is also possible to use a higher gain of the X-ray detector when capturing the diffraction images during the second experiment, relative to the gain used for the first experiment. Another option consists in placing an attenuator in front of the X-ray detector when capturing the diffraction images during the first experiment.

The method may also include a step of processing the first set of images from the pre-experiment to determine experimental parameters for conducting the main experiment. The replacement step may include determining intensities for each of the reflections from the first and second experiments, discarding intensities of topped reflections and scaling and normalizing the resulting intensities.

It is also possible to use at least some of the intensities from the pre-experiment for reflections other than topped reflections or to discard the data from the pre-experiment, depending on how it affects the quality of the resulting output data. Discarding some of the intensity data from the first experiment may be made based on a threshold value.

A method according to the present invention may also include irradiating the crystal sample with an incident X-ray beam during a pre-experiment, and collecting a first set of diffraction images with an X-ray detector having a given dynamic range, the first set of diffraction images providing intensity data of reflections diffracted by the crystal sample. The pre-experiment is preferably conducted in less than five minutes. Data collection parameters (such as unit cell parameters, mosaicity and Bravais class of the crystal sample, I/sigma(I) and exposure time) are then determined, for conducting a main experiment. The main experiment includes irradiating the crystal sample with an incident X-ray beam, and collecting a second set of diffraction images providing higher intensity data of the reflections. Intensities of reflections from the first and second set of diffraction images are then determined and topped reflections that extend beyond the dynamic range of the detector are discarded. Intensities from both the first and second sets of diffraction images are scaled, intensities derived from the first set of images replacing intensities of the discarded topped reflection of the second set of images.

The scaling of the integral intensities is preferably made using a scaling factor determined based on integral intensities of reflections observed in both sets of images. Intensities derived from the first set of data which are below a given threshold can be discarded.

DETAILED DESCRIPTION

Figure 1:
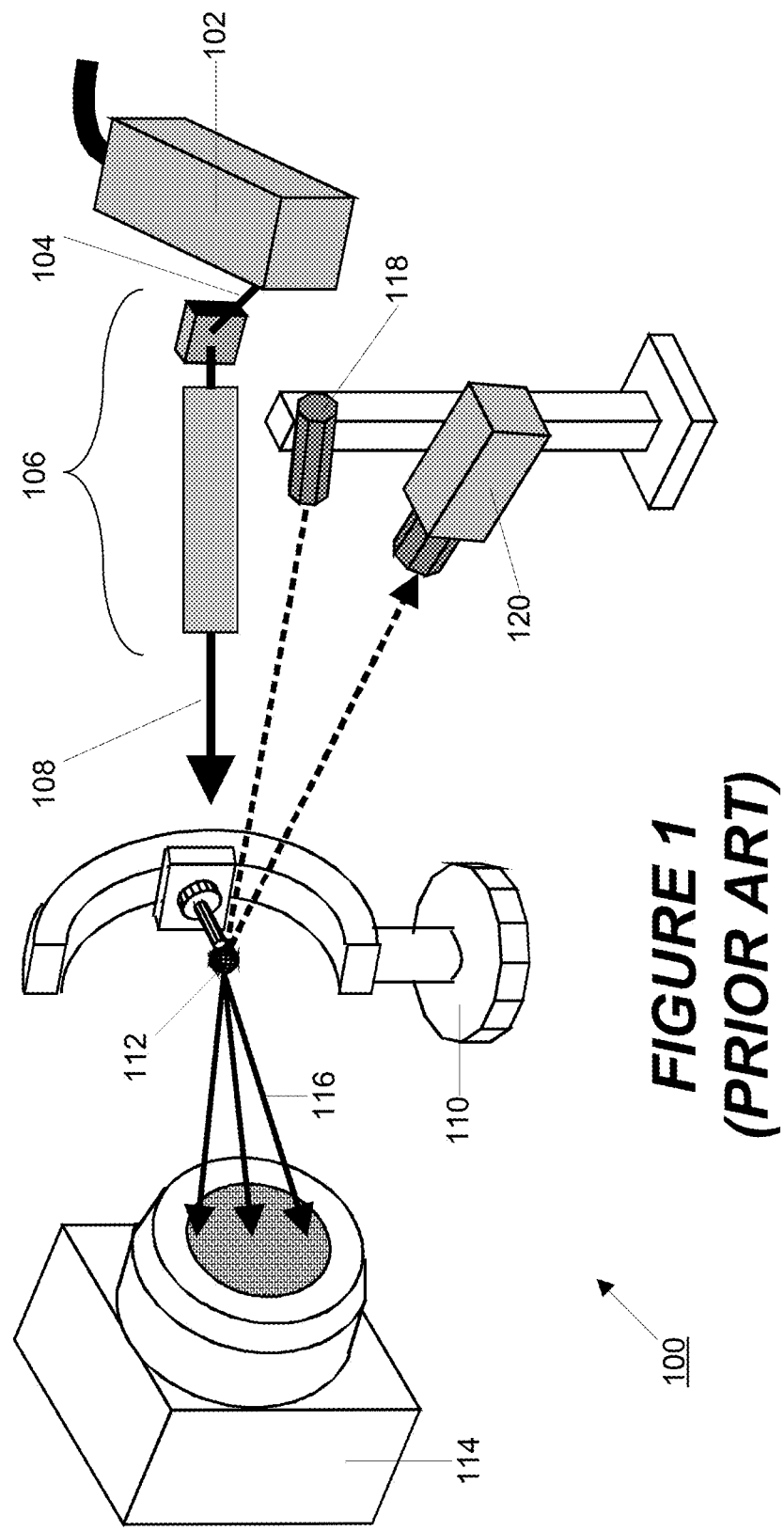
FIG. 1 is a schematic view of a single-crystal X-ray diffraction analysis system according to the prior art.
Figure 2:
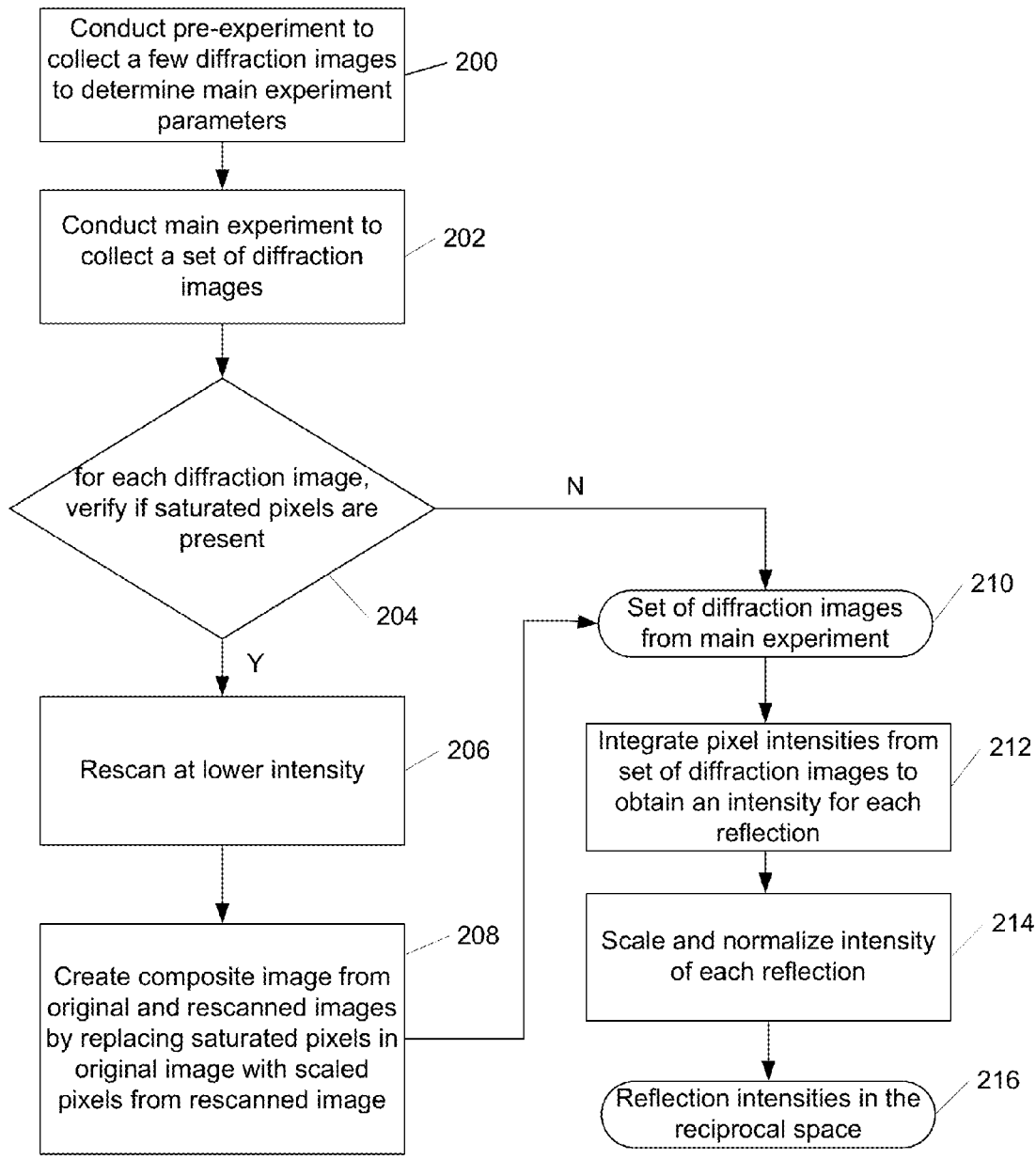
FIG. 2 is a flow diagram showing the steps of the process of performing an X-ray diffraction experiment according to the prior art.

The present invention provides an improved method of conducting an X-ray crystallography analysis. The proposed method takes advantage of a pre-experiment to provide intensity data of reflections appearing as "topped" or "overload" reflections in the main experiment. A "topped" reflection is a reflection which contains at least some pixels having an intensity exceeding a maximum detection limit of the X-ray detector. The dynamic range of the X-ray detector corresponds to the ratio of the maximum and minimal signal the detector can accommodate, the upper limit being referred to as the full-well threshold, above which a pixel cannot accumulate more charges.

In a preferred embodiment, the method includes a step of collecting a first set of diffraction images, also referred to as a first "dataset". This first set of diffraction images is preferably collected during the pre-experiment, and may be used to determine the data collection parameters for the main experiment. The first, pre-experiment uses a fast scan that is preferably sufficient to cover a complete reciprocal sphere of intensity data, with lower diffraction angles, and a short time exposure/image.

A second set of diffraction images, or a second dataset, is collected during a second, main experiment. The main experiment is typically conducted to atomic resolution. By "atomic" resolution, it is meant that a resolution is sufficient to describe details at an atomic level, for example bond lengths and angles between atoms in a molecular structure.

This second set of diffraction images, or second "dataset", also preferably provides for a complete set of intensity data according to the crystal's symmetry. The reflections captured in the second set of diffraction images have higher relative intensities than those produced during the first, pre-experiment.

The information from both datasets is then used to determine the intensity of the individual reflections. This is done by integrating the intensity of the pixels associated with the reflection spots observed in the two sets of diffraction. Since the same crystal sample is used, the same reflections will appear in both datasets, only with different intensities. During or after conducting this step, the intensity data resulting from topped reflections in the main experiment is identified and discarded, and only the intensity data derived from the pre-experiment is present in the combined datasets for these topped reflections.

The intensities from both datasets are then scaled and normalized. The pre-experiment intensities are thus used in replacement of the main experiment intensities for topped reflections. The intensity data derived from the pre-experiment that was not used for topped reflection can be discarded or kept as part of the final output data, depending on whether or not it improves the quality of the final output data. The quality of the output data can be increased, for example, if the ratio I/sigma(I) for the reflections is increased. After completing the integration and scaling steps, and after having decided to keep or discard some or all of the intensity data derived from the pre-experiment, the resulting output data are intensity values for the reflections in the reciprocal space.

The structure of the crystalline compound is described by distinct diffraction intensities collected during the crystallography experiment. A more accurate map of electron density translates into a greater accuracy in the position of the different atoms forming the crystal lattice of the sample.

In contrast with prior art methods, the present invention proposes to replace intensities associated with topped reflections, rather than replacing saturated pixels in the images captured during the experiment. As explained previously, a topped reflection is a reflection having an intensity exceeding the capacity or dynamic range of the X-ray detector.

Figure 3:
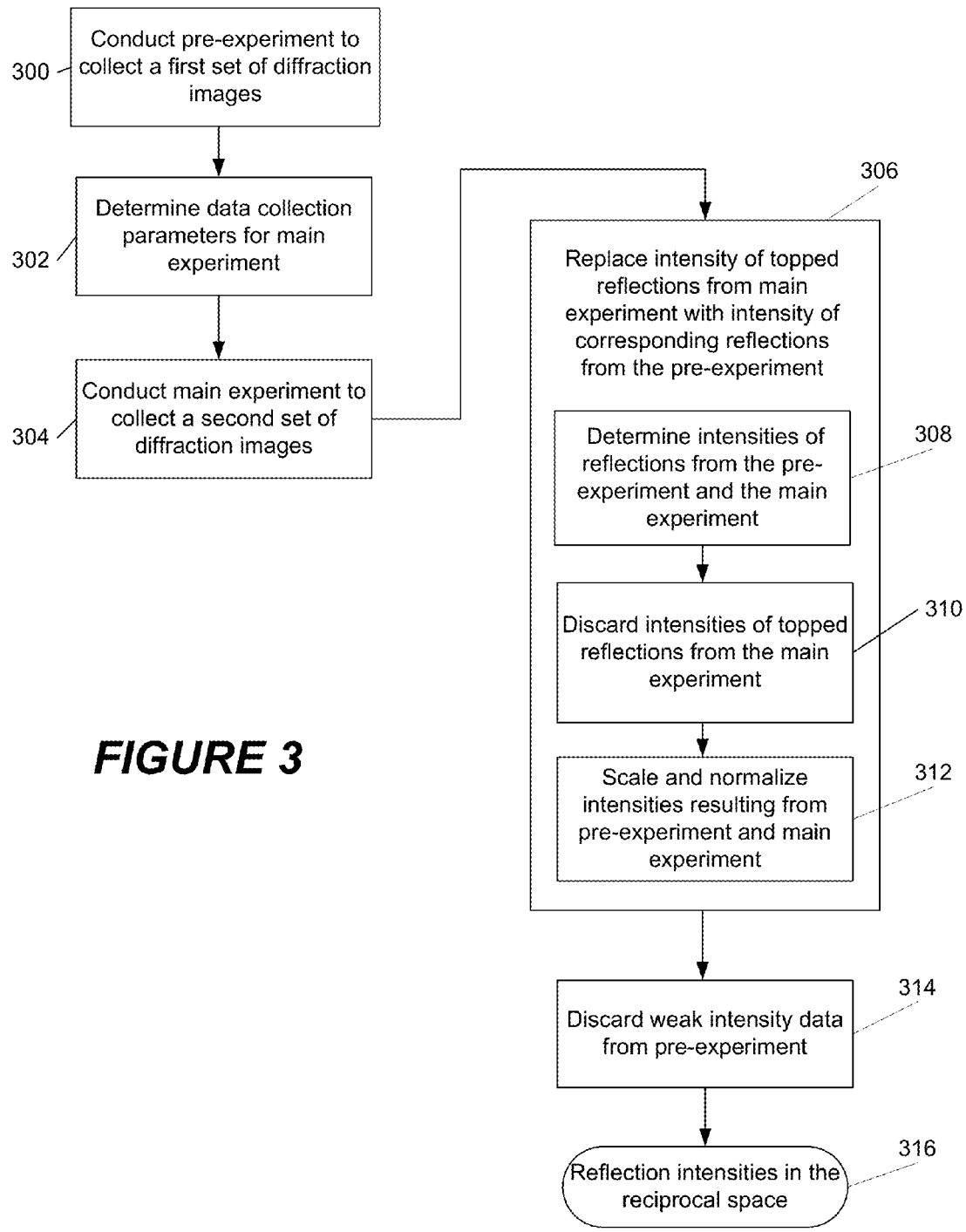
FIG. 3 is flow diagram showing the steps of an exemplary embodiment of the invention.

Referring now to FIG. 3, a flow diagram shows the steps of an exemplary embodiment of the present invention. The method begins with step 300, which consists in conducting a first X-ray diffraction experiment to provide a substantially complete 3D reciprocal sphere of data, resulting from a first set of diffraction images. A person skilled in the art will appreciate that collecting data for at least one hemisphere of the reciprocal space can provide information for the complete reciprocal sphere, given the symmetry of crystalline compounds. By substantially complete, it is meant that intensity data for at least 95% of the reciprocal sphere has been collected. The resolution of this first data set does not need to be to atomic resolution.

This first experiment represents a pre-experiment conducted to determine the data collection parameters to be used during the main, atomic-resolution experiment, which is conducted to determine the 3D structure of the crystalline compound. This pre-experiment, referred to as a "fast scan" experiment, allows one to quickly collect a complete set of diffraction images and provides enough information for determining the appropriate exposure time and the type of data needed for the complete experiment, depending on the system used and the symmetry of the crystal.

During the pre-experiment, the crystalline sample is irradiated by a conditioned X-ray beam, and the constructive interferences of X-ray diffractions scattered by the crystalline compound are captured as reflections by the X-ray detector. The expression "fast scan" refers to the angular speed at which the crystalline compound is moved and to the exposure time used for each frame. While the X-ray detector captures diffraction images, the crystalline compound is moved about a rotational or scanning axis. For example, the crystal sample can be rotated with an angular speed between 0.2°/second to about 3°/second around the phi axis (or between 0.3 and 5 second(s)/degree). The scanning axis typically corresponds to the goniometer's spindle or topmost axis, known in the art as the phi axis. It is also possible to move the crystal about the omega axis. Taking advantage of the deadtime free shutterless acquisition mode of the X-ray detector, the pre-experiment allows for the collection of a complete or substantially complete sphere of data rather rapidly, preferably in less than five minutes. While the pre-experiment is typically conducted in a single scan, it also possible to run two scans to collect the complete first dataset, for cases where a single scan would not allow collecting a complete reciprocal sphere of data, for example if the configuration of the goniometer prevents it, or if the pre-experiment is conducted using an omega scan.

Referring again to FIG. 3, in step 302, the pre-experiment also allows one to determine optimal parameters to be used for the main experiment. These parameters can include, for example, the exposure time to be used for each frame, or the angular/rotational speed of the sample about the scanning axis. Since some compounds diffract X-rays more than others, the exposure time and/or the scan width need to be adjusted for each experiment. The dataset collected during the pre-experiment can be used to determine the main experiment exposure time for a given compound, by analyzing the intensity distribution of the reflections from the pre-experiment, as will be apparent to a person skilled in the art. A rough integration of the reflection intensities is thus conducted to determine the main experiment parameters. For example, the pre-experiment can be used to determine the unit cell parameters, the mosaicity, the Bravais class and/or the I/sigma(I) distribution for optimizing the main experiment. It will be noted that while it is more efficient to conduct a single pre-experiment that allows one to determine the main experiment parameters as well as to collect a complete set of diffraction images, it is also possible to conduct two different pre-experiments, one for determination of the data collection parameters and one for topped reflection replacement.

Once the parameters are determined, the main experiment can be conducted, corresponding to step 304 in the flow diagram. Just as for the pre-experiment, the crystalline compound is irradiated with X-rays while the goniometer rotates the crystal sample relative to the incident X-ray beam and detector. However, this time the crystal is rotated more slowly than during the pre-experiment, generally less than 1°/second, or more than one second per frame. The dataset collected during the main experiment therefore provides intensity information with higher I/sigma(I) than that of the pre-experiment. In other words, the reflections in the main experiment have higher intensities relative to those of the pre-experiment.

In contrast with prior art X-ray diffraction experiments, step 304 is conducted without interruption, that is, without having to simultaneously analyze the images captured to verify whether saturated pixels are present or not. As explained previously, prior art methods required the experiment to be stopped to recapture a new image with a lower intensity (using a beam attenuator or by decreasing the exposure time) when any saturated pixels were detected in an image.

One will appreciate that running an atomic resolution X-ray diffraction experiment can require conducting several runs in order to collect a complete set intensity data. Depending on the symmetry of the crystal and the desired resolution, many runs of data may have to be collected. Each run provides a portion of the complete reciprocal sphere. Performing a few runs is often necessary because the configuration of the goniometer prevents running a full scan without interfering with some of the components of the goniometer. It will also be appreciated that, in some specific cases, a partial scan of the crystalline compound can provide a complete set of data, depending on the sample's symmetry. A set of data is "complete" when the complete contents of the asymmetric unit of the reciprocal space are measured. The reciprocal space asymmetric unit is defined by space group point symmetry plus inversion centre, the so-called Laue symmetry. The completeness of a data set is usually reported as a percentage of observed data, and a data set which is 95% complete is typically considered as a "complete set of data".

When a complete set of data is obtained from the main experiment, the intensity data of topped reflections resulting from detector saturation in the second set of images is replaced with intensity data of corresponding reflections from the first set of images (step 306). In other words, intensities of the topped reflections from the second set of images (collected during the second, main experiment) are replaced with intensities obtained for the corresponding reflections from the first set of images (obtained from the pre-experiment).

Preferably, the first step is to determine the intensity, (also referred as "integral intensity") of each of the respective reflections using the first and second datasets from the pre-experiment and main experiment, respectively, as per step 308 of the flow diagram. While it may be more efficient to integrate intensities from the first and second datasets together, it is possible to integrate intensities from the first/pre-experiment dataset after completing the pre-experiment. Integrating reflection intensities from the first/pre-experiment dataset and from the second/main experiment dataset is performed with existing software tools and includes steps such as the subtraction of background intensities, least squares profile fitting for weaker intensities, and other known correction processing.

The next step consists in discarding the intensity data of topped reflections (step 310). Since the pre-experiment is performed with a faster angular speed, the intensity for a given reflection will be less in the pre-experiment than in the main experiment, and topped pixels in the pre-experiment dataset are unlikely. In contrast, since the main experiment is conducted at a slower angular speed (or longer exposure time/image), saturated pixels can appear. In this case, the data from the saturated pixels is discarded, since is it not reliable. If pixels of a reflection are saturated on all images captured for this reflection, then there is no reliable data for the reflection and the reflection will be missing in the set of data. Depending on the sample's symmetry, a reflection can occur and be observed multiple times during the experiment. In other words, a reflection can appear as saturated on some of the diffraction images but unsaturated in other diffraction images. If a reflection appears with some or with all pixels being saturated, then integral intensity of this occurrence of the reflection is discarded.

Referring now to step 312, the intensities integrated from the pre-experiment data and the main experiment data are scaled together such that reflections from the pre-experiment can be used in replacement of reflections from the main experiment. The intensities determined from the first experiment are scaled and normalized relative to the ones obtained from second experiment. Scaling the pre-experiment reflections with the main experiment reflections is necessary to take into account the different experiment conditions in the two experiments. Since the exposure time of the pre-experiment is much less than the one used for the main experiment, the intensity obtained for a given reflection from the pre-experiment will be much less than the one for the same reflection in the main experiment. In order to determine the proper scaling factor to use, the intensity data for reflections appearing in both experiment datasets is used. Existing software tools are used to scale and normalize the pre-experiment and main experiment intensities.

As can be appreciated, by scaling the first/pre-experiment integral intensities together with the second/main experiment intensities, the missing, topped-out reflections from the main experiment are replaced with corresponding reflections from the pre-experiment. Advantageously, the "fast scan" reflections are obtained from a continuous dataset, which can be easily and reliably reduced to determine the intensity of those reflections appearing as topped reflections in the second set of diffraction images. In addition, the intensities for the fast scan replacement reflections are also reliable, since they correspond to reflections that have saturated in the real experiment runs. In other words, topped reflections from the main experiment are replaced with fast scan reflections for which the intensity is determined with a high confidence.

In step 314 of the method, some or all of the intensity data from the pre-experiment is discarded (i.e. not used). In some cases, it may be decided to keep only the pre-experiment reflections used in replacement of the missing or topped reflections, since the remaining reflections would otherwise deteriorate the data quality of the final output data. In other cases, a greater proportion of the pre-experiment data can be kept in the final output data; intensity data below a given threshold will be discarded and stronger intensities will be kept. The threshold can be, for example, a minimum I/sigma (I) value. Keeping some of the pre-experiment data in the final output can reduce the uncertainties of some of the characteristics related to the crystal structure, such as the distance between the different atoms, for example. Keeping or discarding some or all of the pre-experiment reflections in the final output data depends on factors such as the type of X-ray source, the type of detector and the sample being studied.

Finally, as indicated by block 316 of the flow diagram, the resulting output data of the method provides intensity values for the respective individual reflections diffracted by the crystal sample being studied. In other words, the method provides a complete set of reflection intensities on which an inverse Fourier transform can be applied, each reflection corresponding to a coefficient of the Fourier transform, to determine the structure of the crystalline sample.

As it can be appreciated, the present method not only allows for increasing the dynamic range of the experiment set-up, it also reduces the overall experiment time by using the data collected during the pre-experiment as replacement data for topped reflections. The pre-experiment therefore not only allows determining the data collection parameters to be used for the main, optimized, higher resolution experiment, it also provides replacement data for topped reflections of the higher resolution experiment.

Another advantage of the present invention is that it allows for the recovery of complete reflections, by using intensity information captured before and after the reflections have occurred. Indeed, a reflection spans many images and by replacing intensity data for a reflection, information from several images is used. In contrast, the traditional way of treating topped reflections relies on the collection of a single image, from which a few unsaturated pixels are chosen in replacement of saturated pixels from another experiment.

Those skilled in the art will understand that the steps of the different embodiments of the invention described herein will typically be performed by a data processor as part of a sampling and data collection procedure. Thus, once the system is set up with the desired criteria and a sample crystal properly located therein, it can typically perform the data collection and integration and scaling process without the need for manual intervention by a user.

Although preferred embodiments of the present invention have been described in detail herein and illustrated in the accompanying drawings, it is to be understood that the invention is not limited to these precise embodiments and that various changes and modifications may be effected therein without departing from the present invention.

The invention claimed is:

1. A method of X-ray diffraction-based analysis for determining the structure of a crystal sample, the method comprising the steps of:
    a) conducting a first experiment during which the sample is irradiated with an X-ray beam and a first set of diffraction images is collected by an X-ray detector at different respective rotational positions of the sample, the diffraction images together defining reflections at corresponding intensities;
    b) conducting a second experiment during which the sample is irradiated by an X-ray beam and a second set of diffraction images is collected at different respective rotational positions of the sample, the diffraction images of the second set together defining said reflections with higher relative intensities than those produced during the first experiment, at least some of the diffraction images of the second set including topped reflections resulting from detector saturation; and
    c) replacing intensities of the topped reflections from the second set of images with intensities obtained for the corresponding reflections from the first set of images.

2. The method according to claim 1, wherein a rotational speed of the crystal sample when conducting the second experiment is lower than a rotational speed used for the first experiment.

3. The method according to claim 1, wherein an exposure time of the X-ray detector when capturing the diffraction images during the second experiment is longer than an exposure time used for the first experiment.

4. The method according to claim 1, wherein the first experiment is a pre-experiment and the second experiment is a main experiment, the pre-experiment being conducted prior to the main experiment.

5. The method according to claim 4, further comprising processing the first set of images from the pre-experiment to determine experimental parameters for conducting the main experiment.

6. The method according to claim 1, wherein step c) comprises discarding intensity data of topped reflections.

7. The method according to claim 1, wherein step c) comprises determining intensities for each of the reflections from the first and second experiments.

8. The method according to claim 7, wherein step c) comprises scaling and normalizing the intensities determined from the first experiment relative to those determined from the second experiment.

9. The method according to claim 1, further comprising using at least some of the intensities from the first experiment for reflections other than topped reflections.

10. The method according to claim 1, comprising a step of discarding at least some of the intensities from the first experiment for reflections other than topped reflections.

11. The method according to claim 10, wherein discarding at least some of the intensities from the first experiment is based on a threshold value.

12. The method according to claim 1, wherein the first set of diffraction images is collected during a single scan of the crystal sample while the second set of diffraction images is collected during several scans of the crystal sample.

13. The method according to claim 1, wherein in step a) the first set of diffraction images is collected while rotating the crystal sample with an angular speed between 0.2 degree and 3 degrees per second.

14. The method according to claim 1, wherein in step b), the second set of diffraction images is collected while rotating the crystal sample with an angular speed of one degree per second or less.

15. The method according to claim 1, wherein in steps a) and b), collecting the first and second set of diffraction images is made by rotating the crystal sample about a phi axis of a goniometer in which the sample is mounted.

16. A method of X-ray diffraction-based analysis for determining the structure of a crystal sample, the method comprising the steps of:
    a) irradiating the crystal sample with an incident X-ray beam during a pre-experiment, and collecting a first set of diffraction images with an X-ray detector having a dynamic range at different respective rotational positions of the sample, the first set of diffraction images providing intensity data of reflections diffracted by the crystal sample;
    b) determining data collection parameters from the pre-experiment for conducting a main experiment;
    c) irradiating the crystal sample with an incident X-ray beam during the main experiment, and collecting a second set of diffraction images providing higher intensity data of the reflections at different respective rotational positions of the sample;
    d) determining intensities of reflections from the first and second set of diffraction images;
    e) discarding topped reflections captured with the second set of diffraction images that extend beyond the dynamic range of the detector; and
    f) scaling the intensities from the first set of diffraction images relative to intensities from the second set of diffraction images, intensities from the pre-experiment replacing intensities of the discarded topped reflections from the main experiment.

17. The method according to claim 16, wherein step b) comprises determining at least one of: unit cell parameters, mosaicity and Bravais class of the crystal sample.

18. The method according to claim 16, wherein step b) comprises determining a distribution of intensity to sigma ratio (I/sigma(I)) values.

19. The method according to claim 16, wherein step b) comprises determining a time exposure for the X-ray detector and/or an angular speed of the crystal sample.

20. The method according to claim 16, further comprising discarding intensities derived from the first set of diffraction images which are below a given threshold.

21. The method according to claim 16, wherein step f) comprises using a scaling factor determined based on intensities of reflections observed in both sets of images.

* * * * *